US00PP17134P3

(12) United States Plant Patent
van Dijk

(10) Patent No.: US PP17,134 P3
(45) Date of Patent: Oct. 10, 2006

(54) ***ANTHURIUM ANDREANUM* PLANT NAMED 'ANTHBNZL'**

(50) Latin Name: *Anthurium andreanum L.*
Varietal Denomination: Anthbnzl

(75) Inventor: Jan van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 105 days.

(21) Appl. No.: 10/452,914

(22) Filed: Jun. 3, 2003

(65) Prior Publication Data

US 2005/0015836 P1 Jan. 20, 2005

(51) Int. Cl.
*A01H 5/00* (2006.01)

(52) U.S. Cl. ..... Plt./365
(58) Field of Classification Search ..... Plt./365
See application file for complete search history.

(56) References Cited

PUBLICATIONS

UPOV–ROM Plant Variety Database 2004–04 for cultivar Anthbezel.*

* cited by examiner

*Primary Examiner*—Anne Marie Grunberg
*Assistant Examiner*—Annette H Para
(74) *Attorney, Agent, or Firm*—Foley & Lardner, LLP

(57) ABSTRACT

A new and distinct cultivar of *Anthurium* plant named 'Anthbnzl', as described and illustrated, and particular characterized by the combined features of Compact plant growth and very early and rich flowering; mini-type pot plant, maximum growth to approximately 55 cm; long and erect peduncle, flowers held just above the foliage; open plant habit due to little shoot formation; dark green leaves, durable with light green primary veins; red and very durable flowers, remaining red until they die; and large amount of flowers in relation to the amount of leaves resulting in an excellent leaf to flower size ratio.

4 Drawing Sheets

Latin name of the genus and species of the plant claimed: *Anthurium andreanum* L.
Variety denomination: Anthbnzl.

BACKGROUND OF THE INVENTION

'Anthbnzl' is a new and distinct cultivar of *Anthurium* botanically known as *Anthurium andreanum L.* The new cultivar is a product of a planned breeding program, and was obtained from a cross made during such a program in Bleiswijk, The Netherlands, in 1995.

The female or seed parent was a pink-colored *Anthurium* pot plant identified as number 94-629-06 (unpatented). The male or pollen parent was an orange-colored flowering *Anthurium* pot plant identified as number 95-00-251 (proprietary, unpatented). 'Anthbnzl' was discovered and selected as a flowering plant within the progeny of the stated cross by the inventor, Jan van Dijk, in November 1997 in a controlled environment in a glasshouse in Bleiswijk.

Subsequent asexual reproduction by tissue culture at the same location has demonstrated that the combination of characteristics as herein disclosed for the new cultivar are firmly fixed and are retained through successive generations of asexual reproduction.

BRIEF DESCRIPTION OF THE INVENTION

The following traits have been repeatedly observed and in combination distinguish 'Anthbnzl' as a new and distinct cultivar:

1. Compact plant growth and very early and rich flowering;

2. Mini-type pot plant, maximum growth to approximately 55 cm;
3. Long and erect peduncle, flowers held just above the foliage;
4. Open plant habit due to little shoot formation;
5. Dark green leaves, durable with light green primary veins;
6. Red and very durable flowers, remaining red until they die; and
7. Large amount of flowers in relation to the amount of leaves resulting in an excellent leaf to flower size ratio.

Tabe 1 provides a comparison among plants of 'Anthbnzl' and plants of the parents, 94-629-06 (female parent, unpatented) and 95-00-251 (male parent, proprietary, unpatented):

TABLE 1

| Characteristic | 'Anthbnzl' | 94-629-06 Female Parent | 95-00-251 Male Parent |
|---|---|---|---|
| Growth habit: | Compact, early to flower | Slender, late to flower | Compact, early to flower |
| Leaf description of a mature plant: | Length: 24 cm<br>Width: 13 cm<br>Texture: Flat and mat<br>Color: Yellow-green, RHS 147A | Length: 29 cm<br>Width: 16 cm<br>Texture: Slightly bubbled and mat<br>Color: Green, RHS 139A | Length: 28 cm<br>Width: 15 cm<br>Texture: Flat and mat<br>Color: Green, RHS 137A |
| Spathe description of a mature plant: | Length: 14 cm<br>Width: 14 cm<br>Color: Red, RHS 53B | Length: 17 cm<br>Width: 14 cm<br>Color: Red to pink, RHS 50A | Length: 14 cm<br>Width: 11 cm<br>Color: Orange-red, RHS 34A |

TABLE 1-continued

| Characteristic | 'Anthbnzl' | 94-629-06 Female Parent | 95-00-251 Male Parent |
|---|---|---|---|
| Spadix Description: | Length: 6 cm Width at base: 0.9 cm Color when ripe: Cream yellow, RHS 11D | Length: 9 cm Width at base: 1.2 cm Color when ripe: Red-purple. RHS 58D | Length: 6 cm Width at base: 0.8 cm Color when ripe: Cream yellow, RHS 11D |
| First time of flowering after planting tissue culture: | 36 weeks | 38 weeks | 46 weeks |

Table 2 provides a comparison between plants of 'Anthbnzl' and plants of the closest comparison cultivar *Anthurium andreanum* 'Afrikanerin' (commercially known as Arizona):

TABLE 2

| Characteristic | 'Anthbnzl' | 'Afrikanerin' Closest Comparison Cultivar |
|---|---|---|
| Growth habit: | Compact, early to flower | Slender and open habit, late to flower |
| Leaf description of a mature plant: | Length: 24 cm Width: 13 cm Texture: Flat and mat Color: Yellow-green, RHS 147A | Length: 25 cm Width: 13 cm Texture: Slightly bubbled and glossy Color: Green, RHS 139A |
| Spathe description of a mature plant: | Length: 14 cm Width: 14 cm Color: Red, RHS 53B | Length: 14 cm Width: 13 cm Color: Red, RHS 53B |
| Spadix Description: | Length: 6 cm Width at base: 0.9 cm Color when ripe: Cream yellow, RHS 11D | Length: 7 cm Width at base: 0.8 cm Color when ripe: Cream yellow. RHS 11D |
| First time of flowering after planting tissue culture: | 36 weeks | 40 weeks |

BRIEF DESCRIPTION OF THE DRAWINGS.

The accompanying photographs, taken in Bleiswijk, The Netherlands, show typical 'Anthbnzl' specimens.

FIG. 1 is a side-view of 'Anthbnzl' showing flowers held just above the leaf canopy and showing the open plant structure.

FIG. 2 is a close-up of an 'Anthbnzl' flower showing the spathe and spadix with pollen.

FIG. 3 is a close-up of 'Anthbnzl' flowers at three different stages of development: from young on the left to old on the right. The youngest flower has an unripe spadix (pistils are just visible at the base and pollen is not visible yet). The flower in the middle has a ripe spadix with a small amount of pollen. The spathe of the old flower on the right becomes brown-red, starting in the lobes. Between the left and the right flowers is a difference in age of approximately 8 to 10 weeks.

FIG. 4 is a close-up of the top a young (left) and old leaf blade (right) showing the difference between the vein color of young and old leaf blades. It also shows that the young leaf blades are more shiny then the old leaf blades.

DETAILED BOTANICAL DESCRIPTION

The following observations, measurements and values describe plants grown in Bleiswijk, The Netherlands, under greenhouse conditions, which closely approximate those generally used in horticultural practice.

Color references are made to The Royal Horticultural Society (R.H.S.) Colour Chart, except where general color terms of ordinary significance are used. The color references are approximate, as color depends to a degree on horticultural practices such as light level and degree of fertilization, among others. The color values were determined between 11:00 a.m. and 3:00 p.m. on Mar. 25, 2003, under 5000 lux natural light in a glasshouse in Bleiswijk, The Netherlands. The phenotype may vary significantly when grown under different conditions of temperature, light or other determining factors, without a change in genotype of the plant.

PROPAGATION

Asexual propagation by means of tissue culture and all subsequent propagation that flowered have been true to the original type in plant and flower characteristics.

PLANT DESCRIPTION

Approximately 53–58 weeks following division, 'Anthbnzl' will reach a mature size of approximately 45 cm to 55 cm in height and approximately 35 cm to 45 cm in width in a 17 cm pot.

LEAVES

Form: The leaf blade is elliptical-cordate with an acuminate tip and a cordate base. The leaf blade angle with the petiole between 80 and 110 degrees. 'Anthbnzl' makes larger leaf blades as it ages. 'Anthbnzl' also could produce some axillary shoots with smaller leaf blades. Therefore, a wide range in leaf blade length and width is found on each plant. The minimum leaf blade length is approximately 6 cm and the maximum leaf blade length is approximately 25 cm. The minimum leaf blade width is approximately 4 cm and the maximum leaf blade width is approximately 14 cm.

Texture: The leaf blades are leatherly and thick. The mature leaf blades are weakly cupped.

Veins: The mid-vein and primary veins (the veins which radiate out from the juncture of the petiole and leaf) protude at the underside of the leaf blade. The colour of the veins is light green on the upper side of the leave (RHS 144A) and on the lower side of the leave (RHS 144D). The veins contrast very well with the darker green colour of the leaves.

Leaf blade color: Young leaf blade (approximately maximum 2 weeks old) upper surface is green (RHS 146A). Mature leaf blade (approximately more than 4 weeks upper surface is dark green (RHS 147A) and the lower surface is green (RHS 146A).

Lobes: A leaf blade has two small lobes extending past the petiole. The distance between the petiole and leaf juncture to the highest point on the lobes of mature leaf blades (width 14 cm, length 25 cm) ranges approximately from 5 to 7 cm.

Petiole: The color of the petiole of a mature leaf blade is green (RHS 146A). The petiole color of an immature leaf blade is light green (RHS 144A). The cross section of the petiole is round and the diameter is approximately 3 to 4 mm. The color of the cataphyls surrounding the petioles is green (RHS 143C) with a brown margin (RHS 175A–B).

SPATHE

Buds: The spathe is tightly rolled around the spadix and extrudes from the peduncle sheath. After the spathe is fully open the peduncle elongates for a few more centimeters.

Size: The completely developed spathe of a 50 cm tall plant is approximately 14 cm long and approximately 12 cm to 14 cm wide. The spathe could develop with green lobes or edge, which is not a very stable characteristic throughout the year. If the spathe develops with green lobes or edge, the width of the spathe could increase by some centimeters.

Color: When the spathe is just fully open the upper surface is red (RHS 53B) and the lower surface is grey-red (RHS 179A). Approximately 7 to 8 weeks after the opening of the spathe it starts to discolor to brown-red (RHS 166A), starting with the lobes. After approximately another 16 to 20 weeks the complete flower will be brown. The flowers will stay on the plant for a very long period of time.

Arrangement: The spathe angle to the peduncle is between 80 and 100 degrees. The spathe stand on a straight wiry peduncle approximately 6 cm to 12 cm above the foliage. The peduncle cross-section is round and the diameter approximately 4 mm to 5 mm, depending on the age of the plant. The peduncle is erect and its length depends on the age of the plant. It ranges from approximately 20 to 40 cm.

Shape: The spathe is cordate with a mucronate tip and a cordate base. A just fully opened spathe is slightly cup-shaped. As the flower ages the tip bends upwards slightly. If the spathe develops with green lobes or a green edge the width of the flower is increased considerably.

FLOWERING TIME

One small untreated tissue culture plant of approximately 2 cm tall will flower, depending on season, after approximately 14 to 15 months when approximately 2 to 3 blossoms will appear. More blossoms appear some week later so that a full flowering and salable plant can have 4 to 10 red flowers. Smaller blossoms may occur on less mature growth.

REPRODUCTIVE ORGANS

Size: The spadix measures approximately 5 to 7 cm in height. The length of the spadix is smaller than the length of the spathe. The spadix is a columnar. The width of a mature spadix that is approximately 7 cm long is approximately 10 mm at the base and approximately 8 mm to 9 mm at the top. The spadix angle with spathe is approximately 50 to 70 degrees.

Color: At the time the spathe unrolls the spadix is unripe. Later as the spadix matures, pistils become visible and pollen is produced. An unripe spadix is orange-yellow (RHS 17A) and a ripe spadix is creamy-white (RHS 11D). As the spadix matures (from base to tip) it becomes creamy white. Berries exist on the spadix once pistils have been pollinated.

Berries: The number of berries after pollination could range from 1 up to 400 berries for a spadix on a mature plant. The size of the berries grow from 0.1 cm just after pollination to 0.5 cm after approximately 26 weeks. The berries are round to oblong in shape. The color of the berries ranges from green (RHS 137B) for unripe berries, to brown yellow (RHS 169B to 169C) for ripe berries. The berries normally contain only one seed per berry.

Seeds: The seeds are round to oblong in shape and are slightly flattened off on two sides. The length of the seeds harvested from a large spadix (mature plant size) is about 0.4 cm and the width is about 1.3 mm, depending on the time of the year, cultural conditions and spadix size. The seeds are smooth and slimy in texture. The color of the seeds is grey-orange (RHS 163C), but the color may differ depending on the season and on the ripening stadium of the berry.

Stamens: Anthers and filaments are not clearly visible on the spadix.

Pollen: Large amount of pollen production, white in color.

Pistil: An unripe pistil is orange-yellow (RHS 17A) and a ripe pistil is creamy-white (RHS 11D). The pistil protrudes from the spadix.

ROOTS

Yellow-white roots with smaller hairy laterals. The root-tips are yellow.

Disease/Pest resistance: No known resistance and/or susceptibility to diseases and pests.

I claim:

1. A new and distinct *Anthurium* plant named 'Anthbnzl', as herein described and illustrated.

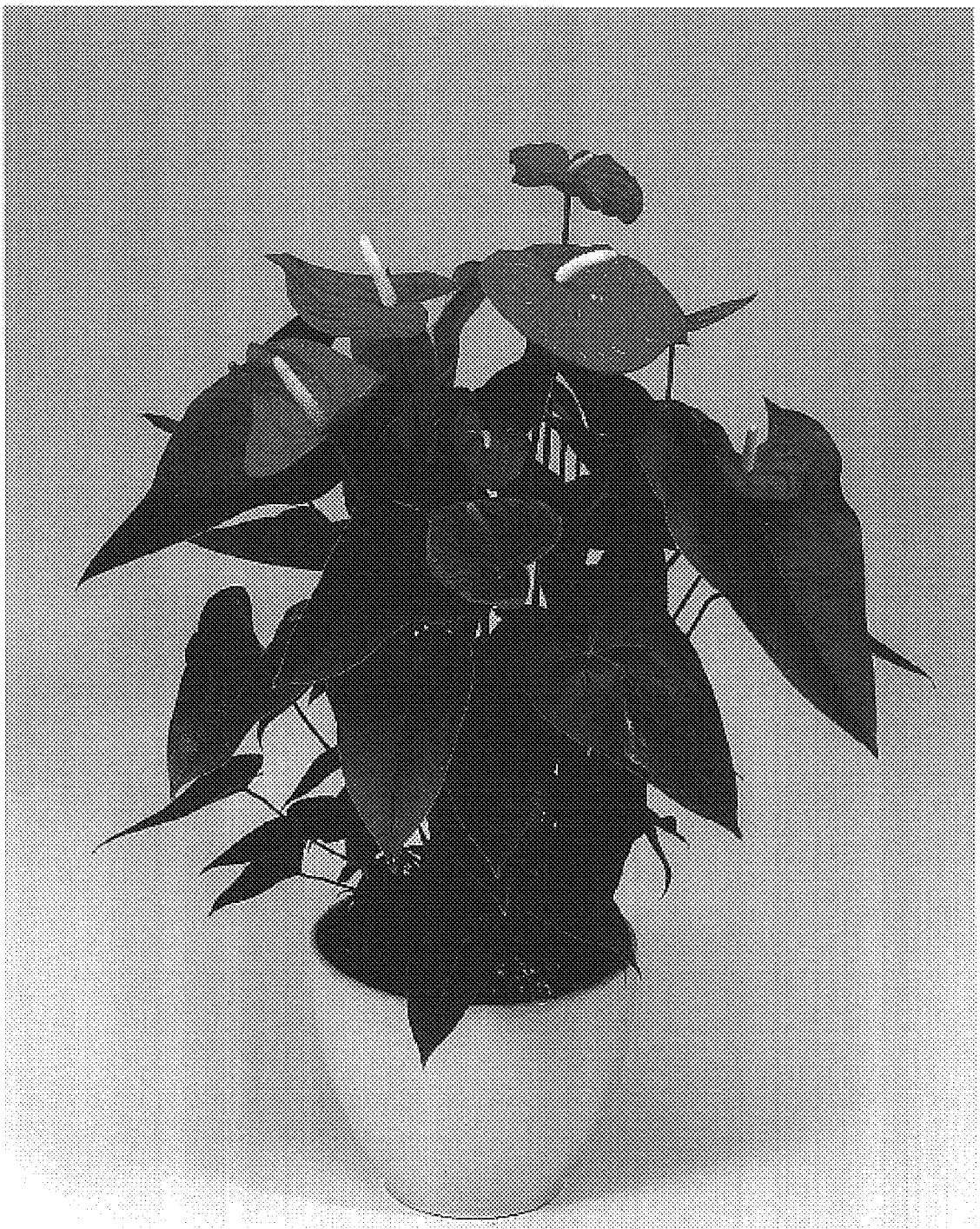

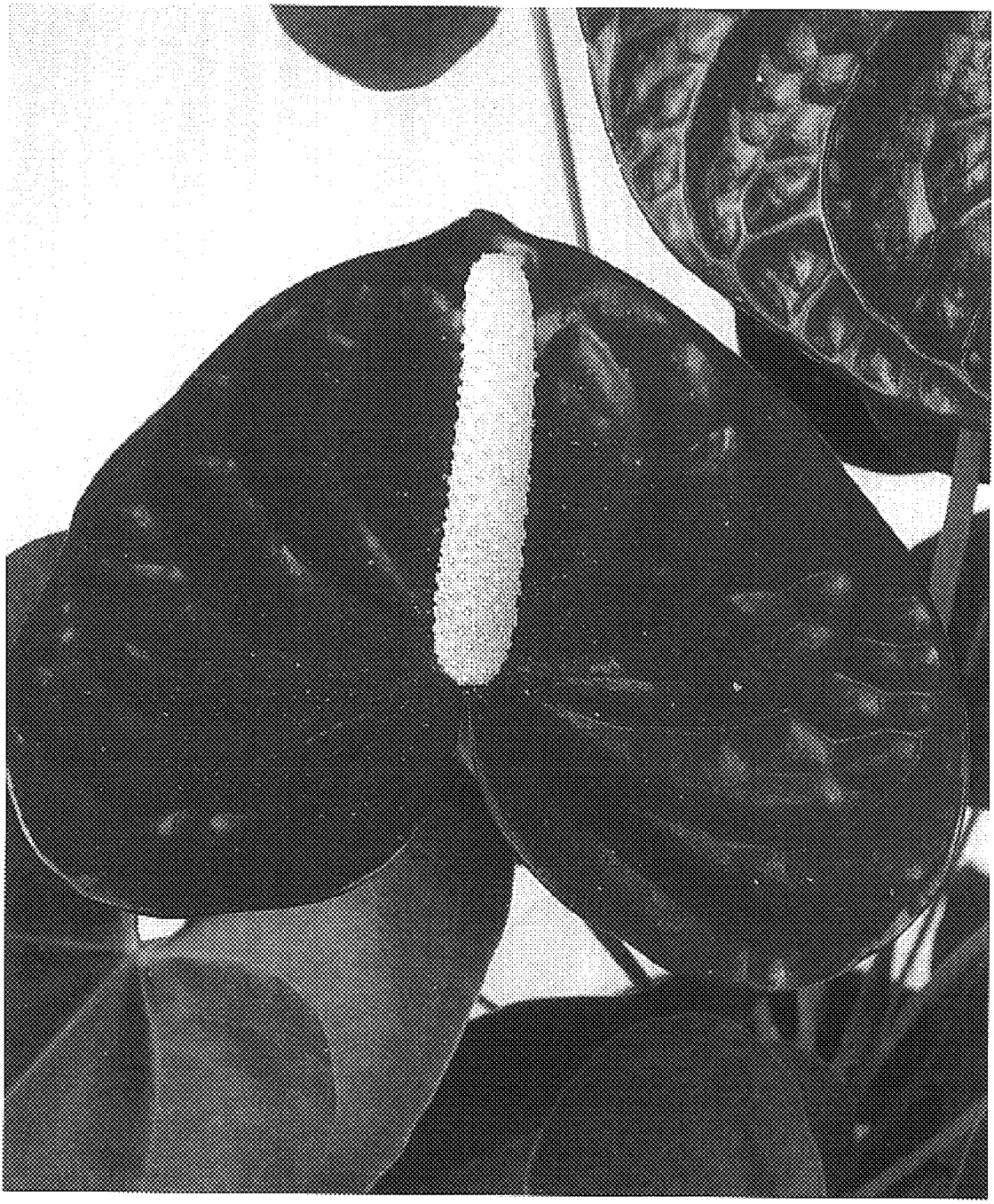

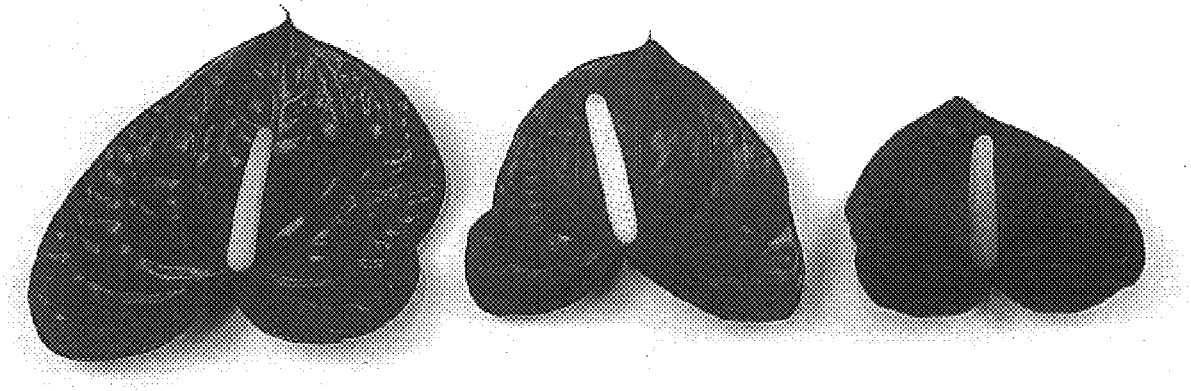

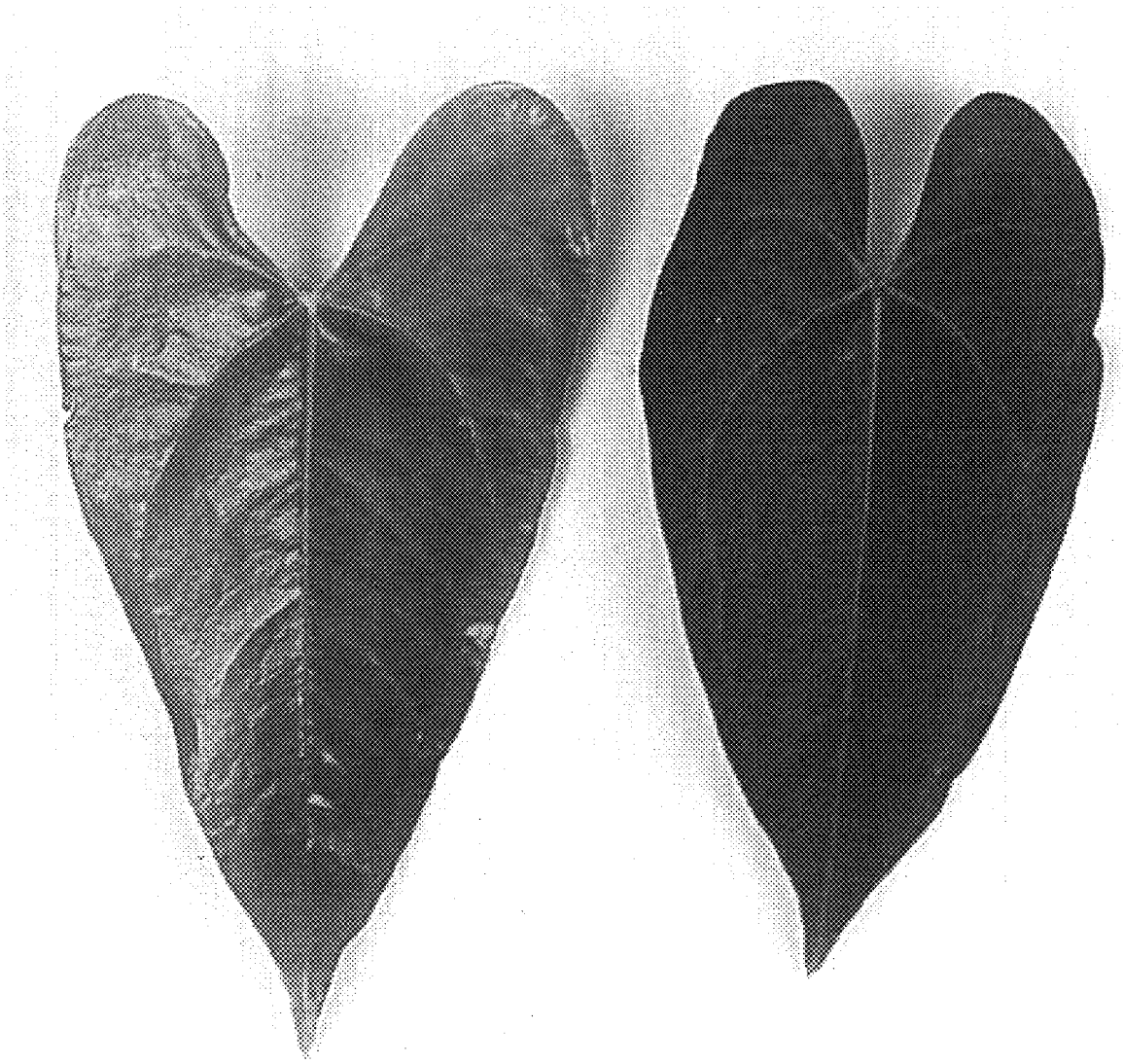

* * * * *